United States Patent [19]

Jung et al.

[11] Patent Number: 5,386,050
[45] Date of Patent: Jan. 31, 1995

[54] (2-ARYLPROPYL)ALKYLSILANES AND THEIR PREPARATION METHODS

[75] Inventors: IL N. Jung; Bok R. Yoo; Bong W. Lee, all of Seoul; Seung H. Yeon, Kyungki-do, all of Rep. of Korea

[73] Assignee: Korea Institute of Science and Technology, Seoul, Rep. of Korea

[21] Appl. No.: 176,433

[22] Filed: Jan. 3, 1994

[51] Int. Cl.$^6$ ............................. C07F 7/08; C07F 7/18
[52] U.S. Cl. .................................. 556/435; 512/440; 512/488; 512/489; 549/215
[58] Field of Search .............. 556/435, 488, 489, 440; 549/215

[56] References Cited

U.S. PATENT DOCUMENTS 5,296,624 3/1994 Larson et al. .................. 556/435

*Primary Examiner*—Paul F. Shaver
*Attorney, Agent, or Firm*—Oblon, Spivak, McClelland, Maier & Neustadt

[57] ABSTRACT

The present invention relates to a process for preparing (2-arylpropyl)alkylsilanes represented by the formula III by reacting (2-arylpropyl)silanes represented by the formula I with olefin compounds represented by the formula II in the presence of hydrosilation catalysts such as chloroplatanic acid, platinum on silica, tributylamine and Pd, Rh, Ni metals.

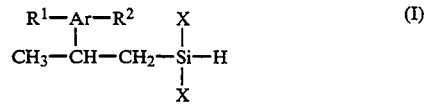

Olefin compounds(cyclohexene or $CH_2=CH-R^3$) (II)

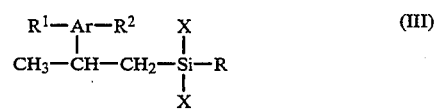

In the formulas (I) and (III), $R^1$ and $R^2$ represent independently hydrogen, alkyl($C_1$-$C_4$), fluoro, chloro or bromo; and Ar represents phenyl ring, naphthalene ring, or biphenyl ring. X represents hydrogen or chloro group. In the formula (III), R represents $-(CH_2CH_2)-R^3$, sec-butyl, or cyclohexyl wherein $R^3$=Ph, $CH_2Cl$, $C_nH_{2n}CH_3$ (n=0-15), $CH_2Si(Me)_mCl_{3-m}$ (m=0-3), $(CH_2)_2Si(Me)_m(OMe)_{3-m}$ (m=0-3), $(CH_2)_3Si(Me)_m(OMe)_{3-m}$ (m=0-3), $Si(Me)_mCl_{3-m}$ (m=0-3), $CF_3$, CN, $CH_2CN$,

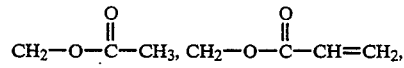

$CH=CH_2$, $(CH_2)_4CH=CH_2$,

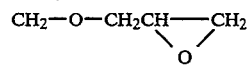

or Ph—$CH_2Cl$.

31 Claims, No Drawings

(2-ARYLPROPYL)ALKYLSILANES AND THEIR PREPARATION METHODS

FIELD OF THE INVENTION

The present invention relates to (2-arylpropyl) alkylsilanes represented by the formula III, and a process for the preparation of the compounds of formula III comprising reacting (2-arylpropyl)silanes represented by the formula I with olefin compounds represented by the formula II in the presence of hydrosilation catalysts such as chloroplatanic acid, platinum on silica, tributylamine and Pd, Rh, Ni metals.

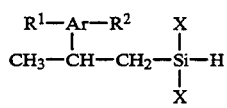
(I)

Olefin compounds (cyclohexene or $CH_2=CH-R^3$)     (II)

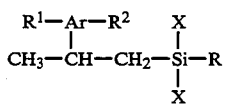
(III)

In the formulas (I) and (III), $R^1$ and $R^2$ represent independently hydrogen, alkyl ($C_1$-$C_4$), fluoro, chloro or bromo; and Ar represents phenyl ring, naphthalene ring, or biphenyl ring. X represents hydrogen or chloro group. In the formula (III), R represents—$(CH_2CH_2)$—$R^3$, sec-butyl, or cyclohexyl wherein $R^3$ is Ph, $CH_2Cl$, $C_nH_{2n}CH_3$ (n=0–15), $CH_2Si(Me)_mCl_{3-m}$ (m=0–3), $(CH_2)_2Si(Me)_m(OMe)_{3-m}$ (m=0–3), $(CH_2)_3Si(Me)_m(OMe)_{3-m}$ (m=0–3), $Si(Me)_mCl_{3-m}$ (m=0–3), $CF_3$, $CN$, $CH_2CN$,

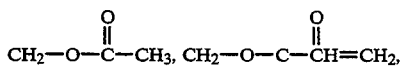

$CH=CH_2$, $(CH_2)_4CH=CH_2$,

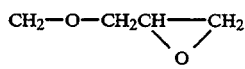

or Ph-$CH_2Cl$.

DESCRIPTION OF THE PRIOR ART

Hurd reported first the direct synthesis of allyldichlorosilane from allyl chloride and metallic silicon in 1945 (D. T. Hurd, J. Am. Chem. Soc., 87, 1813 (1945)). When allyl chloride was reacted with a 9:1 Si—Cu alloy, a vigorous exothermic reaction occurred even at 250° C. The condensates obtained contained trichlorosilane, tetrachlorosilane, allyldichlorosilane, diallyldichlorosilane, and allyltrichlorosilane predominates due to the decomposition of allyl chloride during the reaction. However, this reaction has never been used on a large scale in industry, because of the decomposition of allyl chloride and the easy polymerization of diallyldichlorosilane at high temperature above 130° C.

Mironov and Zelinskii reported later that they obtained only 644 g of a mixture of allylchlorosilanes from the reaction of a 5:1 Si—Cu alloy with 2 kg of allyl chloride at 300° C. The product mixture contained 356 g of allyldichlorosilane, 185 g of allyltrichlorosilane, and 103 g of diallydichlorosilane (V. M. Mironov and D. N. Zelinskii, Isvest. Akad. Nauk S.S.S.R,. Otdel. Khim. Nauk, 383 (1957)). The production of allyldichlorosilane and allyltrichloro-silane indicates that allyl chloride decomposed under the reaction conditions and dehydrochlorination or dechlorination were accompanied. This is why the yield was under 30%, indicating that the process was not economically feasible.

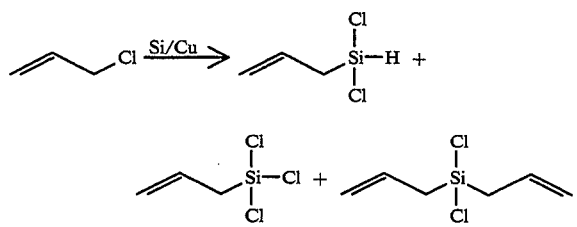

We reported a preparation method of allylchlorosilanes by directly reacting silicon metal simultaneously with allyl chloride and hydrogen chloride in the presence of copper catalyst at a temperature from 220°0 C. to 350° C. Allyldichlorosilane was obtained as the major product indicating one mole of each reactant reacted with the same silicon atom. When sufficient hydrogen chloride was added, diallyldichlorosilane was not Formed. This eliminated the polymerization problem involved in the direct synthesis (Korean Patent application 92-10292 (92. 6. 13)).

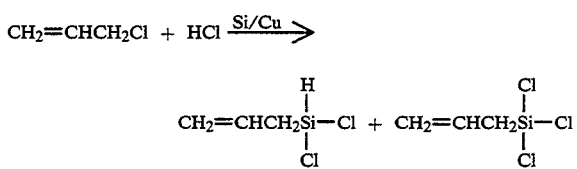

Nametkin and his co-workers reported that the Friedel-Crafts type addition of allylchlorosilanes to mono substituted benzenes in order to give 3-phenyl-1-silabutane (N. S. Namerkin, V. M. Vdovin, E. S. Finkelshtein, V.D. Oppengeium, and N. A. Chekalina, Izv. Akad. Nauk SSSR, Set. Khim. , 1966 (11) , 1998–2004). They reacted allyltrichlorosilane, allyldichlorosilane, allylmethyldichlorosilane, or allyltrimethylsilane with benzene, chlorobenzene, bromobenzene, or benzyltrichlorosilane in the presence of aluminum chloride to give 2-phenylpropylsilanes. The yield of 2-(phenyl)-propyldichlorosilane from the reaction of allyldichlorosilane with benzene was 60%.

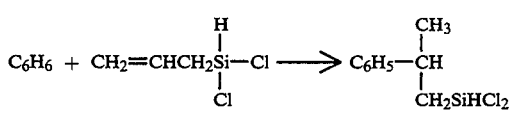

The present inventors reported the preparation method of (2-arylpropyl)dichlorosilane represented by the formula (I) by the Frieden-Crafts alkylation of various substituted aromatic compounds with allyldichlorosilane in the presence of Lewis acid catalysts (Korean Patent application 92-12996 (92. 7. 21)).

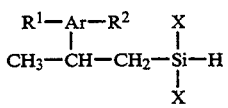

The present inventors also reported a process for preparing new organochlorosilanes by the hydrosilation reaction of Si—H bond containing bissilylalkanes with olefin compounds in the presence of catalysts such as chloroplatinic acid, platinum on silica, tributylamine and Pd, Rh, Ni metals (Korean Patent application 92-12998 (92. 7.21)).

SUMMARY OF THE INVENTION

The present invention relates to (2-arylpropyl) alkylsilanes represented by the formula III and a process for the preparation of the compounds of formula III comprising reacting (2-arylpropyl)silanes represented by the formula I with olefin compounds represented by the formula II in the presence of hydrosilation catalysts such as chloroplatanic acid, platinum on silica, tributylamine and Pd, Rh, Ni metals.

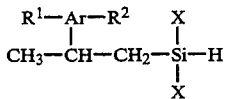

Olefin compounds( cyclohexene or $CH_2=CH-R^3$)
(II)

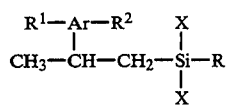

In the formulas (I) and (III), $R^1$ and $R^2$ represent independently hydrogen, alkyl($C_1$–$C_4$), fluoro, chloro or bromo; and Ar represents phenyl ring, naphthalene ring or biphenyl ring. X represents hydrogen or chloro group. In the formula (III), R represents —($CH_2CH_2$)—$R^3$, sec-butyl, or cyclohexyl wherein $R^3$ is Ph, $CH_2Cl$, $C_nH_{2n}CH_3$ (n=0–15), $CH_2Si(Me)_mCl_{3-m}$ (m=0–3), $(CH_2)_2Si(Me),(OMe)_{3-m}$ (m=0–3), $(CH_2)_3Si(Me)_m (OMe)_{3-m}$ (m=0–3), $Si(Me)_mCl_{3-m}$ (m=0–3), $CF_3$, $CN$, $CH_2CN$,

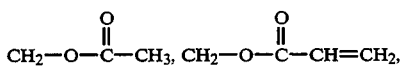

$CH=CH_2$, $(CH_2)_4CH=CH_2$,

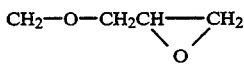

or Ph-$CH_2Cl$.

The (2-arylpropyl)alkyldichlorosilane producing hydrosilation reactions of the present invention can be run in standard laboratory glasswares or commercial equipments, under inert atmosphere, with units for external heating and cooling, stirring, and for incremental addition of the start-silanes or olefins. The reaction can be carried out in most of organic solvents, but is also proceeds in neat condition. When allyl chloride is hydrosilated, the reactor should be pressurized because propylene gas is evolved as a by-product.

In a typical preparation, (2-arylpropyl)dichlorosilane and the hydrosilation catalyst are placed in the reactor under inert atmosphere. The olefin compound is then slowly added to the solution with stirring. The reactions may be sufficiently exothermic at controlled addition rates to maintain to reflux without continuously carrying out external heating. After completion of addition, heating may be carried out for a certain period of time to complete the hydrosilation and then the products may be fractionally distilled at atmosphere or under vacuum.

The invention will be further illustrated by the following examples. It is, however, not intended that this invention will be limited by the examples.

EXAMPLE 1

To a 500 ml, three neck, round bottomed flask equipped with a mechanical stirrer, a dropping funnel, and a reflux condenser, 6.0 g (0.03 mole) of 3-phenyl-1,1-dichloro-1-silabutane, 6.28 g (0.09 mole) of allyl chloride, and 150 µl of 1% chloroplatinic acid in isopnopanol were placed under the dry nitrogen atmosphere. The flask was then immersed in a hot water bath of 45°–50° C. The solution was stirred vigorously for three hours. Gas chromatography analysis showed that no silane was Left. Vacuum distillation of the solution gave 2.21. g (bp, 111°–2° C./0.6 mmHg) of 1,4,4-trichloro-6-phenyl-4-silaheptane and 2.63 g of 3-phenyl-1,1,1-trichloro-1-silabutane. Besides these products, a small amount of 4,4-dichloro-2-phenyl-4-silaheptane was also obtained.

EXAMPLE 2 in the same apparatus and procedures as EXAMPLE 1, 5.0 g (0.023 mole) of 3-phenyl-1,1-dichloro-1-silabutane, 5.8 g (0.07 mole) of 1-hexene, and 100 µl of 1% chloroplatinic acid in isopropanol were placed and reacted under the dry nitrogen atmosphere. Vacuum distillation of the reaction products gave 4.23 g (bp, 115°–8° C./0.6 mmHg) of 4,4-dichloro-2-phenyl-4-siladecane.

EXAMPLE 3

In the same apparatus and procedures as EXAMPLE 1, 10.0 g (0.046 mole) of 3-phenyl-1,1-dichloro-1-silabutane, 7.2 g (0.07 mole) of styrene, and 20 µl of 1% chloroplatinic acid in isopropanol were placed and reacted for 3 hours under the dry nitrogen atmosphere at 60° C. Vacuum distillation of the reaction products gave 11.0 g (bp, 133°–5° C./0.6 mmHg) of 3,3-dichloro-1,5-diphenyl-3-silahexane.

EXAMPLE 4

In the same apparatus and procedures as EXAMPLE 1, 10.0 g (0.046 mole) of 3-phenyl-1,1-dichloro-1-silabutane, 6.9 g (0.065 mole) of methyldichlorovinylsilane, and 120 µl of 1% chloroplatinic acid in isopropanol were placed and reacted for 3 hours under the dry nitrogen atmosphere. Vacuum distillation of the reaction products gave 9.0 g (bp, 117°–9° C./0.6 mmHg ) of 2,2,5,5-tetrachloro-7-phenyl-2,5-disilaoctane.

EXAMPLE 5

In the same apparatus and procedures as EXAMPLE 1, 6.3 g (0.027 mole) of 3-(3- or 4-methylphenyl)-1,1-dichloro-1-silabutane, 8.26 g (0.11 mole) of allyl chloride, and 100 μl of 1% chloroplatinic acid in isopropanol were placed and refluxed under the dry nitrogen atmosphere for 11.5 hours. Vacuum distillation of the reaction products gave 2.6 g (bp, 115°–8° C./0.6 mmHg) of 1,4,4-trichloro-6-(3- or 4-methylphenyl)-4-silaheptane.

EXAMPLE 6

In the same apparatus and procedures as EXAMPLE 1, 6.0 g (0.023 mole) of 3-(3- or 4-methylphenyl)-1,1-dichloro-1-silabutane. 4.4 g (0.05 mole) of 1-hexene, and 100 μl of 1% chloroplatinic acid in isopropanol were placed and refluxed under the dry nitrogen atmosphere for 3 hours. Vacuum distillation of the reaction products gave 2.6 g (bp, 115°–8° C./0.6 mmHg) of 4,4-trichloro-6-(3- or 4-methylphenyl)-4-silaheptane.

EXAMPLE 7

In the same apparatus and procedure as EXAMPLE 1, 7.5 g (0.03 mole) of 3-(3- or 4-ethylphenyl)-1,1-dichloro-1-silabutane, 9.3 g (0.12 mole) of allylchloride, and 150 μl of 1% chloroplatinic acid in isopropanol were placed and refluxed under the dry nitrogen atmosphere for 1.5 hours. Vacuum distillation of the reaction products gave 3.2 g (bp, 120°–3° C./0.6 mmHg) of 1,4,4-trichloro-6-(3- or 4-ethylphenyl)-4-silaheptane.

EXAMPLE 8

In the same apparatus and procedure as EXAMPLE 1, 6.4 g (0.018 mole) of 3-(3- or 4-isopropylphenyl)-1,1-dichloro-1-silabutane, 5.2 g (0.072 mole) of allylchloride, and 100 μl of 1% chloroplatinic acid in isopropanol were placed and refluxed under the dry nitrogen atmosphere for 1.5 hours. Vacuum distillation of the reaction products gave 2.6 g (bp, 115°–8° C./0.6 mmHg) of 1,4,4-trichloro-6-(3- or 4-isopropylphenyl)-4-silaheptane.

EXAMPLE 9

In the same apparatus and procedures as EXAMPLE 1, 5.5 g (0.03 mole) of 3-(2- or 4-fluorophenyl)-1,1-dichloro-1-silabutane, 7.1 g (0.09 mole) of allyl chloride, and 150 μl of 1% chloroplatinic acid in isopropanol were placed and refluxed under the dry nitrogen atmosphere for 3 hours. Vacuum distillation of the reaction products gave 2.9 g (bp, 111°–4° C./0.6 mmHg) of 1,4,4-trichloro-6-(2- or 4-fluorophenyl)-4-silaheptane.

EXAMPLE 10

In the same apparatus and procedures as EXAMPLE 1, 7.5 g (0.03 mole) of 3-(2- or 4-chlorophenyl)-1,1-dichloro-1-silabutane, 4.5 g (0.044 mole) of allyl chloride, and 50 μl of 1% chloroplatinic acid in isopropanol were placed and refluxed under the dry nitrogen atmosphere for 3 hours. Vacuum distillation of the reaction products gave 2.9 g (bp, 135°–7° C./0.6 mmHg) of 1,4,4-trichloro-6-(2- or 4-chlorophenyl)-4-silaheptane.

The structure and NMR data of the hydrosilated products prepared as above are listed in Table. I

TABLE I

The structure and $^1$H-NMR data of 3-(substituted aryl)propyldichlorosilanes

| Substituents | | CH$_3$(d) | CH(hex.) | CH$_2$(m) | aryl-H(m) | R$^1$ and R | Remark |
|---|---|---|---|---|---|---|---|
| R$^1$ | R | | | | | | |
| H | (CH$_2$)$_3$Cl | 1.45 | 3.21 | 1.61–1.69 | 7.20–7.41 | 0.72–0.91(m, 1H, CH$_2$), 1.77–1.91(m, 2H, CH$_2$), 3.42(t, 2H, CH$_2$) | Example 1 |
| H | (CH$_2$)$_2$CH$_3$ | 1.40 | 3.18 | 1.47–1.65 | 7.20–7.39 | 0.73–0.77(m, 2H, CH$_2$), 0.89(t, 3H, CH$_3$), 1.23–1.40(m, 2H, CH$_2$) | |
| H | (CH$_2$)$_5$CH$_3$ | 1.40 | 3.16 | 1.48–1.63 | 7.20–7.35 | 0.72–0.77(m, 2H, CH$_2$), 0.90(t, 3H, CH$_3$), 1.21–1.37(m 8H, CH$_2$) | Example 3 |
| H | (CH$_2$)$_{11}$CH$_3$ | 1.39 | 3.16 | 1.47–1.64 | 7.19–7.36 | 0.72–0.78(m, 2H, CH$_2$), 0.92(t, 3H, CH$_3$), 1.21–1.37(m 20H, CH$_2$) | |
| H | (CH$_2$)$_{17}$CH$_3$ | 1.39 | 3.15 | 1.47–1.64 | 7.20–7.36 | 0.72–0.78(m, 2H, CH$_2$), 0.92(t, 3H, CH$_3$), 1.21–1.37(m 36H, CH$_2$) | |
| H | c-hexyl | 1.44 | 3.20 | 1.49–1.62 | 7.22–7.38 | 0.64–0.74(m, 1H, CH), 1.11–1.37(m, 4H, CH$_2$), 1.57–1.93(m, 6H, CH$_2$) | |
| H | (CH$_2$)$_2$CN* | 1.45 | 3.21 | 1.58–1.69 | 7.19–7.38 | 0.83–0.95(m, 2H, CH$_2$), 2.48(t, 2H, CH$_2$) | Example 16 |
| H | (CH$_2$)$_3$CN | 1.45 | 3.21 | 1.58–1.69 | 7.19–7.38 | 0.84–1.48(m, 4H, CH$_2$), 2.49(t, 2H, CH$_2$) | |
| H | 2-butenyl | 1.43 | 3.22 | 1.49–1.68 | 7.16–7.34 | 1.49–1.63(d, 3H, CH$_3$), 2.10–2.37(m, 2H, CH$_2$), 5.29–5.72(m, 2H, CH) | |
| H | 7-octenyl | 1.42 | 3.21 | 1.47–1.67 | 7.14–7.34 | 0.72–0.84(m, 2H, CH$_2$), 1.21–1.37(m, 8H, CH$_2$), 1.90–2.19(m, 2H, CH$_2$), 4.80–5.10(m, 2H, CH$_2$), 5.48–6.10(m, 1H, CH) | |
| H | (CH$_2$)$_2$Ph | 1.40 | 3.16 | 1.47–1.63 | 7.04–7.35 | 1.07–1.16 and 2.62–2.70(m, 2H, CH$_2$), 7.04–7.35(m, 5H, aryl-H) | Example 3 |
| H | C$_2$H$_4$—⌬—CH$_2$Cl | 1.40 | 3.16 | 1.48–1.62 | 7.03–7.33 | 1.08–1.15 and 2.60–2.70(m, 2H, CH$_2$), 7.03–7.33(m, 4H, aryl-H), 4.53(s, 2H, CH$_2$) | |
| H | (CH$_2$)$_2$CF$_3$ | 1.41 | 3.21 | 1.48–1.64 | 7.17–7.37 | 0.71–0.78, 1.69–1.82 and 2.03–2.37(m, 6H, CH$_2$) | |
| H | (CH$_2$)$_2$CF$_3$ | 1.40 | 3.20 | 1.48–1.62 | 7.16–7.35 | 0.71–0.79 and 2.00–2.34(m, 2H, CH$_2$) | |
| H | c-hexenyl-ethyl | 1.43 | 3.22 | 1.48–1.61 | 7.19–7.33 | 0.74–0.82(m, 2H, CH$_2$), 1.48–2.23(m, 9H, CH$_2$ and CH), 5.51–5.73(m, 2H, CH) | |
| H | (CH$_2$)$_3$SiMe$_3$ | 1.40 | 3.20 | 1.48–1.62 | 7.10–7.36 | 0.01(s, 9H, CH$_3$), 0.61–0.60, 1.08–1.16 and 1.53–1.64(m, 2H, CH$_2$) | |
| H | (CH$_2$)$_3$SiMe$_3$ | 1.40 | 3.19 | 1.46–1.61 | 7.09–7.36 | 0.01(s, 9H, CH$_3$), 0.60–0.64 and 1.06–1.15(m, 2H, CH$_2$) | |
| H | (CH$_2$)$_3$SiMe$_2$Cl | 1.40 | 3.20 | 1.48–1.61 | 7.10–7.37 | 0.40(s, 6H, CH$_3$), 0.79–1.21(m, 4H, CH$_2$) | |
| H | (CH$_2$)$_3$SiMe$_2$Cl | 1.40 | 3.19 | 1.46–1.61 | 7.10–7.37 | 0.41(s, 6H, CH$_3$), 0.78–1.21(m, 4H, CH$_2$) | |
| H | (CH$_2$)$_2$SiMeCl$_2$ | 1.40 | 3.19 | 1.47–1.62 | 7.18–7.36 | 0.80(s, 3H, CH$_3$), 1.10–1.22(m, 2H, CH$_2$), 1.47–1.62(m, 2H, CH$_2$) | Example 4 |
| H | (CH$_2$)$_2$SiMeCl$_2$ | 1.40 | 3.18 | 1.47–1.63 | 7.13–7.35 | 0.79(s, 3H, CH$_3$), 1.08–1.24(m, 4H, CH$_2$) | |
| H | (CH$_2$)$_3$SiCl$_3$ | 1.41 | 3.20 | 1.48–1.63 | 7.14–7.36 | 1.01–1.77(m, 6H, CH$_2$) | |
| H | (CH$_2$)$_3$SiCl$_3$ | 1.40 | 3.19 | 1.46–1.61 | 7.12–7.37 | 1.08–1.64(m, 4H, CH$_2$) | |
| 3-Me | (CH$_2$)$_3$Cl | 1.41 | 3.15 | 1.57–1.62 | 7.07–7.27 | 0.71–0.95 and 1.71–1.83(m, 2H, CH$_2$), 2.37(s, 3H, CH$_3$), 3.40(t, 2H, CH$_2$) | Example 5 |
| 4-Me | (CH$_2$)$_3$Cl | 1.42 | 3.15 | 1.57–1.64 | 7.07–7.27 | 0.71–0.95 and 1.71–1.83(m, 2H, CH$_2$), 2.39(s, 3H, CH$_3$), 3.40(t, 2H, CH$_2$) | Example 5 |
| 3-Me | (CH$_2$)$_3$SiMe$_2$Cl | 1.40 | 3.16 | 1.49–1.61 | 7.08–7.36 | 0.40(s, 6H, CH$_3$), 2.36(s, 3H, CH$_3$), 0.76–1.20(m, 4H, CH$_2$) | |
| 4-Me | (CH$_2$)$_3$SiMe$_2$Cl | 1.41 | 3.16 | 1.49–1.61 | 7.08–7.36 | 0.41(s, 6H, CH$_3$), 2.37(s, 3H, CH$_3$), 0.76–1.20(m, 4H, CH$_2$) | |
| 3-Me | (CH$_2$)$_2$SiMeCl$_2$ | 1.41 | 3.16 | 1.56–1.63 | 7.09–7.30 | 0.79 and 2.38(s, 3H, CH$_3$), 1.08–1.23(m, 4H, CH$_2$) | |

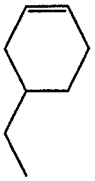

TABLE I-continued

The structure and $^1$H-NMR data of 3-(substituted aryl)propyldichlorosilanes $$\text{Structure: } CH_3\text{-}SiCl_2\text{-}CH_2\text{-}CH(R)\text{-}CH_2\text{-}C_6H_4\text{-}R^1$$

| Substituents | | CH$_3$(d) | CH(hex.) | CH$_2$(m) | aryl-H(m) | R$^1$ and R | Remark |
|---|---|---|---|---|---|---|---|
| R$^1$ | R | | | | | | |
| 4-Me | (CH$_2$)$_2$SiMeCl$_2$ | 1.42 | 3.16 | 1.56–1.63 | 7.09–7.30 | 0.80 and 2.39(s, 3H, CH$_3$), 1.08–1.23(m, 4H, CH$_2$) | |
| 3-Me | (CH$_2$)$_2$SiCl$_3$ | 1.41 | 3.15 | 1.55–1.63 | 7.08–7.31 | 0.98–1.76(m, 4H, CH$_2$) and 2.37(s, 3H, CH$_3$) | |
| 4-Me | (CH$_2$)$_2$SiCl$_3$ | 1.42 | 3.15 | 1.55–1.63 | 7.08–7.31 | 0.99–1.76(m, 4H, CH$_2$) and 2.38(s, 3H, CH$_3$) | |
| 3-Me | (CH$_2$)$_5$CH$_3$ | 1.37 | 3.11 | 1.57–1.62 | 7.03–7.27 | 0.60–0.78(m, 2H, CH$_2$), 0.88(t, 2H, CH$_2$), 1.15–1.61(m, 8H, CH$_2$), 2.33(s, 3H, CH$_3$) | Example 6 |
| 4-Me | (CH$_2$)$_5$CH$_3$ | 1.38 | 3.11 | 1.57–1.62 | 7.03–7.27 | 0.60–0.78(m, 2H, CH$_2$), 0.88(t, 2H, CH$_2$), 1.15–1.61(m, 8H, CH$_2$), 2.35(s, 3H, CH$_3$) | Example 6 |
| 3-Me | c-hexyl | 1.42 | 3.18 | 1.41–1.62 | 7.05–7.35 | 0.64–0.72(m, 1H, CH), 1.10–1.35(m, 4H, CH$_2$), 1.56–1.91(m, 6H, CH$_2$), 2.34(s, 3H, CH$_3$) | |
| 4-Me | c-hexyl | 1.43 | 3.18 | 1.41–1.62 | 7.05–7.35 | 0.64–0.72(m, 1H, CH), 1.10–1.35(m, 4H, CH$_2$), 1.56–1.91(m, 6H, CH$_2$), 2.35(s, 3H, CH$_3$) | |
| 3-Me | (CH$_2$)$_2$Ph | 1.38 | 3.16 | 1.43–1.61 | 7.03–7.33 | 1.05–1.14 and 2.60–2.68(m, 2H, CH$_2$), 7.03–7.33(m, 5H, aryl-H), 2.34(s, 3H, CH$_3$) | |
| 4-Me | (CH$_2$)$_2$Ph | 1.39 | 3.16 | 1.43–1.61 | 7.03–7.33 | 1.05–1.14 and 2.60–2.68(m, 2H, CH$_2$), 7.03–7.33(m, 5H, aryl-H), 2.35(s, 3H, CH$_3$) | |
| 3-Et | (CH$_2$)$_3$Cl | 1.41 | 3.15 | 1.57–1.62 | 7.08–7.27 | 0.74–0.82 and 1.72–1.80(m, 2H, CH$_2$), 1.26(t, 3H, CH$_3$), 3.37(q, 2H, CH$_2$) | Example 7 |
| 4-Et | (CH$_2$)$_3$Cl | 1.42 | 3.15 | 1.57–1.62 | 7.08–7.27 | 0.74–0.82 and 1.72–1.80(m, 2H, CH$_2$), 1.27(t, 3H, CH$_3$), 3.38(q, 2H, CH$_2$) | Example 7 |
| 3-Et | (CH$_2$)$_2$CH$_3$ | 1.38 | 3.12 | 1.51–1.55 | 7.04–7.27 | 0.87 and 1.24(t, 3H, CH$_3$), 1.39(t, 3H, CH$_3$), 1.28–1.38(m, 2H, CH$_2$), 2.64(q, 2H, CH$_2$) | |
| 4-Et | (CH$_2$)$_2$CH$_3$ | 1.40 | 3.31 | 1.54–1.60 | 7.19–7.45 | 1.12–1.28 and 1.67–1.79(m, 2H, CH$_2$), 2.80(q, 2H, CH$_2$), 7.19–7.45(m, 5H, Phenyl-H) | |
| 4-Et | (CH$_2$)$_2$Ph | 1.40 | 3.31 | 1.54–1.60 | 7.19–7.45 | 1.12–1.28 and 1.67–1.79(m, 2H, CH$_2$), 2.81(q, 2H, CH$_2$), 7.19–7.45(m, 5H, Phenyl-H) | |
| 3-Et | (CH$_2$)$_2$SiMeCl$_2$ | 1.41 | 3.16 | 1.55–1.63 | 7.08–7.29 | 0.79 and 1.25(s, 3H, CH$_3$), 1.08–1.23(m, 4H, CH$_3$), 1.26(t, 3H, CH$_3$), 2.82(q, 2H, CH$_2$) | |
| 4-Et | (CH$_2$)$_2$SiMeCl$_2$ | 1.42 | 3.16 | 1.55–1.63 | 7.08–7.29 | 0.80 and 1.26(s, 3H, CH$_3$), 1.08–1.23(m, 4H, CH$_2$), 1.27(t, 3H, CH$_3$), 2.83(q, 2H, CH$_2$) | 3 |
| 3-Et | (CH$_2$)$_2$SiCl$_3$ | 1.41 | 3.15 | 1.54–1.62 | 7.06–7.31 | 0.97–1.75(m, 4H, CH$_2$), 1.25(t, 3H, CH$_3$), 2.81(q, 2H, CH$_2$) | |
| 4-Et | (CH$_2$)$_2$SiCl$_3$ | 1.42 | 3.15 | 1.54–1.62 | 7.06–7.31 | 0.97–1.76(m, 4H, CH$_2$), 1.26(t, 3H, CH$_3$), 2.82(q, 2H, CH$_2$) | |
| 3-Et | (CH$_2$)$_6$CH$_3$ | 1.36 | 3.11 | 1.55–1.61 | 7.04–7.25 | 0.60–0.74(m, 2H, CH$_2$), 0.88 and 1.24(t, 3H, CH$_3$), 1.13–1.61(m, 8H, CH$_2$), 2.81(q, 2H, CH$_2$) | |
| 4-Et | (CH$_2$)$_6$CH$_3$ | 1.37 | 3.16 | 1.55–1.61 | 7.04–7.25 | 0.60–0.74(m, 2H, CH$_2$), 0.88 and 1.24(t, 3H, CH$_3$), 1.13–1.61(m, 8H, CH$_2$), 2.82(q, 2H, CH$_2$) | |
| 3-Et | c-hexyl | 1.41 | 3.17 | 1.40–1.61 | 7.04–7.32 | 0.64–0.72(m, 1H, CH), 1.23(t, 3H, CH$_3$), 1.09–1.33(m, 4H, CH$_2$), 1.54–1.89(m, 6H, CH$_2$), 2.81(q, 2H, CH$_2$) | |
| 4-Et | c-hexyl | 1.42 | 3.17 | 1.40–1.61 | 7.04–7.32 | 0.64–0.72(m, 1H, CH), 1.24(t, 3H, CH$_3$), 1.09–1.33(m, 4H, CH$_2$), 1.54–1.89(m, 6H, CH$_2$), 2.81(q, 2H, CH$_2$) | |
| 3-i-Pr | (CH$_2$)$_3$Cl | 1.41 | 3.16 | 1.57–1.62 | 6.95–7.30 | 0.72–0.79 and 1.71–1.78(m, 2H, CH$_2$), 1.28(d, 6H, CH$_3$), 2.92(hept. 1H, CH), 3.36(t, 2H, CH$_2$) | Example 8 |
| 4-i-Pr | (CH$_2$)$_3$Cl | 1.43 | 3.17 | 1.57–1.62 | 6.95–7.30 | 0.72–0.79 and 1.71–1.78(m, 2H, CH$_2$), 1.29(d, 6H, CH$_3$), 2.93(hept. 1H, CH), 3.37(t, 2H, CH$_2$) | Example 8 |
| 3-i-Pr | (CH$_2$)$_6$CH$_3$ | 1.40 | 3.16 | 1.56–1.61 | 7.01–7.27 | 0.60–0.73(m, 2H, CH$_2$), 0.88(t, 3H, CH$_3$), 1.11–1.60(m, 8H, CH$_2$), 1.25(d, 6H, CH$_3$), 2.89(hept, 1H, CH) | |
| 4-i-Pr | (CH$_2$)$_6$CH$_3$ | 1.41 | 3.16 | 1.56–1.61 | 7.01–7.27 | 0.60–0.73(m, 2H, CH$_2$), 0.88(t, 3H, CH$_3$), 1.11–1.60(m, 8H, CH$_2$), 1.26(d, 6H, CH$_3$), 2.91(hept, 1H, CH) | |
| 3-i-pr | (CH$_2$)$_2$SiMeCl$_2$ | 1.39 | 3.16 | 1.54–1.63 | 7.04–7.28 | 0.78, (s, 3H, CH$_3$), 1.08–1.23(m, 4H, CH$_2$), 1.26(d, 6H, CH$_3$), 2.90(hept., 1H, CH) | |
| 4-i-pr | (CH$_2$)$_2$SiMeCl$_2$ | 1.41 | 3.16 | 1.54–1.63 | 7.04–7.28 | 0.79, (s, 3H, CH$_3$), 1.08–1.23(m, 4H, CH$_2$), 1.27(d, 6H, CH$_3$), 2.91(hept., 1H, CH) | |
| 3-i-pr | (CH$_2$)$_2$SiCl$_3$ | 1.40 | 3.15 | 1.55–1.61 | 7.01–7.34 | 1.02–1.63(m, 4H, CH$_2$), 1.27(d, 6H, CH$_3$), 2.91(hept, 1H, CH) | |
| 4-i-pr | (CH$_2$)$_2$SiCl$_3$ | 1.42 | 3.16 | 1.55–1.61 | 7.01–7.34 | 1.02–1.63(m, 4H, CH$_2$), 1.28(d, 6H, CH$_3$), 2.92(hept, 1H, CH) | |
| 3-Ph | (CH$_2$)$_3$Cl | 1.46 | 3.24 | 1.59–1.64 | 7.27–7.61 | 0.79–0.91 and 1.76–1.94(m, 2H, CH$_2$), 3.25(t, 2H, CH$_2$), 7.27–7.61(m, 5H, phenyl-H) | |

TABLE I-continued

The structure and $^1$H-NMR data of 3-(substituted aryl)propyldichlorosilanes $$\text{structure: } R^1\text{-C}_6H_4\text{-CH}_2\text{-CH(CH}_3\text{)-CH}_2\text{-Si(Cl)}_2\text{-R}$$

| Substituents | | NMR data(ppm) | | | | | Remark |
|---|---|---|---|---|---|---|---|
| $R^1$ | R | $CH_3(d)$ | CH(hex.) | $CH_2(m)$ | aryl-H(m) | $R^1$ and R | |
| 4-Ph | $(CH_2)_3Cl$ | 1.47 | 3.24 | 1.59-1.64 | 7.27-7.61 | 0.79-0.91 and 1.76-1.94(m, 2H, $CH_2$), 3.26(t, 2H, $CH_2$), 7.27-7.61(m, 5H, phenyl-H) | |
| 2-F | $(CH_2)_3Cl$ | 1.39 | 3.18 | 1.54-1.59 | 7.00-7.30 | 0.86-1.09(m, 2H, $CH_2$), 1.80-1.93(m, 2H, $CH_2$), 3.45(t, 2H, $CH_2$) | Example 9 |
| 4-F | $(CH_2)_3Cl$ | 1.44 | 3.18 | 1.54-1.59 | 7.00-7.30 | 0.94-1.01(m, 2H, $CH_2$), 1.80-1.93(m, 2H, $CH_2$), 3.45(t, 2H, $CH_{26}$) | Example 9 |
| 2-F | $(CH_2)_2SiMeCl_2$ | 1.39 | 3.20 | 1.51-1.59 | 7.04-7.28 | 1.11-1.27 and 1.67-1.75(m, 2H, $CH_2$) | |
| 4-F | $(CH_2)_2SiMeCl_2$ | 1.40 | 3.19 | 1.51-1.59 | 7.04-7.28 | 1.11-1.27 and 1.67-1.75(m, 2H, $CH_2$) | |
| 2-Cl | $(CH_2)_3Cl$ | 1.38 | 3.73 | 1.53-1.59 | 7.13-7.42 | 0.88-1.00 and 1.77-1.90(m, 2H, $CH_2$), 3.43(t, 2H, $CH_2$) | Example 10 |
| 4-Cl | $(CH_2)_3Cl$ | 1.39 | 3.15 | 1.53-1.59 | 7.12-7.37 | 0.88-1.00 and 1.77-1.90(m, 2H, $CH_2$), 3.45(t, 2H, $CH_2$) | Example 10 |
| 2-Cl | $(CH_2)_5CH_3$ | 1.37 | 3.71 | 1.48-1.52 | 7.12-7.37 | 0.73-0.82(m, 2H, $CH_2$), 0.89(t, 3H, $CH_3$), 1.23-1.44(m 8H, $CH_2$,) | |
| 4-Cl | $(CH_2)_5CH_3$ | 1.39 | 3.13 | 1.48-1.52 | 7.09-7.34 | 0.73-0.82(m, 2H, $CH_2$), 0.89(t, 3H, $CH_3$), 1.23-1.44(m 8H, $CH_2$,) | |
| 2-Cl | $(CH_2)_2SiCl_3$ | 1.39 | 3.69 | 1.49-1.58 | 7.09-7.34 | 1.08-1.65(m, 4H, $CH_2$) | |
| 4-Cl | $(CH_2)_2SiCl_3$ | 1.40 | 3.18 | 1.49-1.58 | 7.03-7.45 | 1.08-1.65(m, 4H, $CH_2$) | |
| 2-Br | $(CH_2)_3Cl$ | 1.37 | 3.70 | 1.53-1.58 | 7.03-7.45 | 0.87-1.00 and 1.76-1.90(m, 2H, $CH_2$), 3.43(t, 2H, $CH_2$) | |
| 4-Br | $(CH_2)_3Cl$ | 1.38 | 3.12 | 1.53-1.58 | 7.02-7.44 | 0.87-1.00 and 1.76-1.90(m, 2H, $CH_2$), 3.44(t, 2H, $CH_2$) | |
| 2-Br | $(CH_2)_2SiMe_3$ | 1.37 | 3.70 | 1.47-1.60 | 7.02-7.44 | 0.62-0.68 and 1.08-1.16(m, 2H, $CH_2$) | |
| 4-Br | $(CH_2)_2SiMe_3$ | 1.39 | 3.20 | 1.47-1.60 | 7.02-7.44 | 0.62-0.68 and 1.08-1.16(m, 2H, $CH_2$) | |

*Nickel metal used as the catalyst

EXAMPLE 11

In the same apparatus and procedures as EXAMPLE 1, 8.5 g (0.034 mole of 3-(2,5-dimethylphenyl)-1,1-dichloro-1-silabutane, 8.7 g (0.10 mole) of 1-hexene, and 120 μl of 1% chloroplatinic acid in isopropanol were placed and refluxed under the dry nitrogen atmosphere for 3 hours. Vacuum distillation of the reaction products gave 7.4 g (bp, 130°-3° C./0.6 mmHg) of 4,4-dichloro-2-(2,5-dimethylphenyl)-4-siladecane.

EXAMPLE 12

In the same apparatus and procedures as EXAMPLE 1, 10.0 g (0.034 mole) of 3-(1-naphthyl)-1,1-dichloro-1-silabutane, 11.4 g (0.15 mole) of allylchloride, and 180 μl of 1% chloroplatinic acid in isopropanol were placed and refluxed under the dry nitrogen atmosphere for 3 hours. Vacuum distillation of the reaction products gave 4.2 g (bp, 158°-160° C./0.6 mmHg) of 1,4,4-trichloro-6-(1- or 2-naphthyl)-4-silaheptane.

The structures and NMR data of the compounds prepared using the same procedure as described in EXAMPLE 11 and 12 are listed in Table II.

TABLE II

The structure and $^1$H-NMR data of 3-(aryl with two substituents)propyldichlorosilanes

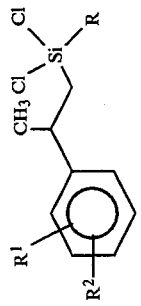

| Substituents | | | | | | | NMR data(ppm) | |
|---|---|---|---|---|---|---|---|---|
| $R^1$ | $R^2$ | R | $CH_3(d)$ | CH(hex.) | $CH_2(m)$ | aryl-H(m) | $R^1$, $R^2$ and R | Remark |
| 2-Me | 5-Me | $(CH_2)_3Cl$ | 1.43 | 3.16 | 1.57–1.62 | 7.07–7.26 | 0.59–0.75 and 1.72–1.83(m, 2H, $CH_2$), 2.35 and 2.37(s, 3H, $CH_3$), 3.39(t, 2H, $CH_2$) | Example 11 |
| 2-Me | 5-Me | $(CH_2)_5CH_3$ | 1.33 | 3.39 | 1.45–1.63 | 6.91–7.26 | 0.67–0.82(m, 2H, $CH_2$), 0.88(s, 3H, $CH_3$), 1.17–1.32(m, 8H, $CH_2$), 2.32 and 2.33(s, 3H, $CH_3$) | |
| 2-Me | 5-Me | $(CH_2)_{17}CH_3$ | 1.33 | 3.34 | 1.43–1.63 | 6.92–7.26 | 0.66–0.81(m, 2H, $CH_2$), 0.88(s, 3H, $CH_3$), 1.16–1.33(m, 36H, $CH_2$), 2.31 and 2.32(s, 3H, $CH_3$) | |
| 3-Me | 4-Me | $(CH_2)_2Ph$ | 1.46 | 3.18 | 1.38–1.55 | 7.00–7.40 | 1.05–1.17 and 2.64–2.74(m, 2H, $CH_2$), 2.32 and 2.32(s, 3H, $CH_3$), 7.00–7.40(m, 5H, phenyl-H) | |
| 3-Me | 4-Me | $(CH_2)_2CN$* | 1.46 | 3.19 | 1.42–1.59 | 7.11–7.39 | 0.82–0.94(m, 2H, $CH_2$), 2.33 and 2.34(s, 3H, $CH_3$), 2.47(t, 2H, $CH_2$) | |
| 2-Me | 5-Me | c-hexyl | 1.42 | 3.18 | 1.47–1.63 | 7.19–7.36 | 0.67–0.75(m, 1H, CH), 1.10–1.34(m, 4H, $CH_2$), 1.56–1.93(m, 6H, $CH_2$), 2.33 and 2.35(s, 3H, $CH_3$) | |
| 2-Me | 5-Me | $(CH_2)_2SiMe_2Cl$ | 1.41 | 3.16 | 1.51–1.62 | 7.07–7.26 | 0.41(s, 6H, $CH_3$)0.77–1.19(m, 4H, $CH_2$), 2.34 and 2.36(s, 3H, $CH_3$) | |
| 2-Me | 5-Me | $(CH_2)_2SiMeCl_2$ | 1.42 | 3.16 | 1.53–1.61 | 7.05–7.27 | 0.79(s, 3H, $CH_3$), 0.58–0.74 and 1.46–1.63(m, 2H, $CH_2$), 2.36 and 2.39(s, 3H, $CH_3$) | |
| 2-Me | 5-Me | $(CH_2)_2SiCl_3$ | 1.41 | 3.17 | 1.53–1.60 | 7.04–7.28 | 0.97–1.74(m, 4H, $CH_2$), 2.36 and 2.37(s, 3H, $CH_3$) | |
| 2,3-dibenzo | | $(CH_2)_3Cl$ | 1.61 | 4.13 | 1.66–1.91 | 7.27–8.24 | 0.90–0.96 and 1.66–1.91(m, 2H, $CH_2$), 3.37(t, 2H, $CH_2$), 7.27–8.24(m, 4H, $(CH)_4$) | Example 12 |
| 3,4-dibenzo | | $(CH_2)_3Cl$ | 1.54 | 4.13 | 1.66–1.91 | 7.27–8.24 | 0.84–0.92 and 1.66–1.91(m, 2H, $CH_2$), 3.27(t, 2H, $CH_2$), 7.27–8.24(m, 4H, $(CH)_4$) | Example 12 |

*Nickel metal used as the catalyst.

EXAMPLE 13

In the same apparatus and procedures as EXAMPLE 1, 6.0 g (0.027 mole) of 3-phenyl-1,1-dichloro-1-silabutane, 4.1 g (0.05 mole) of cyclohexene, and 90 μl of 1% chloroplatinic acid in isopropanol were placed under the dry nitrogen atmosphere. The reactor was sealed and the solution was stirred for 3 hours. Vacuum distillation of the reaction products gave 7.4 g (bp, 157°–9° C./0.05 mmHg) of 1-cyclohexyl-1,1-dichloro-3-phenyl-1-silabutane.

EXAMPLE 14

In the same apparatus and procedure as EXAMPLE 1, 6.2 g (0.027 mole) of 3-(2,5-dimethylphenyl)-1,1-dichloro-1-silabutane, 5.4 g (0.05 mole) of styrene, and 90 μl of 1% chloroplatinic acid in isopropanol were placed and refluxed under the dry nitrogen atmosphere for 3 hours. Vacuum distillation of the reaction products gave 7.4 g (bp, 139°–141° C./0.6 mmHg) of 3,3-dichloro-5-(2,5-dimethylphenyl)-1-phenyl-3-silahexane.

The structures and NMR data of the compounds prepared using the same procedure as described in EXAMPLE 13 and 14 are listed in Table III.

TABLE III

The structure and $^1$H-NMR data of 3-(aryl with one substituent)propyp-1,1-dimethoxysilanes Structure:

Me  MeO  OMe
  \  |  /
   Si—R
   |
   CH₂
   |
   CH
   |
   (aryl)—R₁

| Substituents | | CH₃(d) | CH(hex.) | CL₂(d) | aryl-H (m) | OCH₃(s) | NMR data (ppm) R₁ and R | Remark |
|---|---|---|---|---|---|---|---|---|
| R₁ | R | | | | | | | |
| H | (CH₂)₃Cl | 1.37 | 2.99 | 1.07 | 7.18–7.38 | 3.36, 3.48 | 0.46–0.60(m, 1H, CH₂), 0.91(m, 2H, CH₂), 3.42(t, 2H, CH₂) | Example 13 |
| H | (CH₂)₂CH₃ | 1.32 | 3.00 | 1.06 | 7.16–7.33 | 3.35, 3.48 | 0.46–0.61(m, 2H, CH₂), 0.90(t, 3H, CH₃), 1.22–1.37 (m, 2H, CH₂) | |
| H | (CH₂)₂CH₃ | 1.33 | 2.98 | 1.05 | 7.15–7.35 | 3.44, 3.49 | 0.45–0.60(m, 2H, CH₂), 0.89(t, 3H, CH₃), 1.21–1.37(m 8H, CH₂) | |
| H | (CH₂)₁₁CH₃ | 1.32 | 2.98 | 1.05 | 7.14–7.33 | 3.43, 3.48 | 0.44–0.60(m, 2H, CH₂), 0.89(t, 3H, CH₃), 1.21–1.36(m 20H, CH₂) | |
| H | (CH₂)₁₇CH₃ | 1.32 | 2.98 | 1.05 | 7.17–7.34 | 3.43, 3.47 | 0.44–0.61(m, 2H, CH₂), , 0.89(t, 3H, CH₃), 1.21–1.36(m 36H, CH₂) | |
| H | c-hexyl | 1.36 | 3.02 | 1.04 | 7.17–7.38 | 3.48, 3.50 | 0.63–0.78(m, 1H, CH), 1.10–1.29(m, 4H, CH₂), 1.64–1.82(m, 6H, CH₂) | |
| H | 2-butenyl | 1.33 | 3.02 | 1.06 | 7.19–7.38 | 3.37, 3.48 | 0.56–0.67(m, 2H, CH₂), 2.47(t, 2H, CH₂) | |
| H | 2-butenyl | 1.36 | 3.03 | 1.08 | 7.16–7.37 | 3.38, 3.49 | 1.46–1.61(d, 3H, CH₃), 2.10–2.36(m, 2H, CH₂), 5.28–5.71(m, 2H, CH) | |
| H | 7-octenyl | 1.32 | 2.98 | 1.05 | 7.15–7.35 | 3.41, 3.48 | 0.44–0.61(m, 2H, CH₂), 1.21–1.36(m, 8H, CH₂), 1.90–2.19(m, 2H, CH₂), 4.81–5.10(m, 2H, CH₂), 5.48–6.10(m, 1H, CH) | |
| H | (CH₂)₂Ph | 1.33 | 2.99 | 1.05 | 7.06–7.34 | 3.38, 3.47 | 0.47–0.59 and 2.60–2.69(m, 2H, CH₂), 7.06–7.34(m, 5H, aryl-H) | |
| H | (CH₂)₃CF₃ | 1.34 | 3.00 | 1.03 | 7.12–7.36 | 3.34, 3.49 | 0.48–0.64 and 2.03–2.37(m, 2H, CH₂) | |
| H | (CH₂)₂CF₃ | 1.40 | 3.02 | 1.04 | 7.16–7.35 | 3.35, 3.49 | 0.46–0.60 and 2.00–2.33(m, 4H, CH₂) | |
| H | (CH₂)₃O₂CCH₃ | 1.33 | 2.99 | 1.05 | 7.05–7.29 | 3.42, 3.38 | 0.57(t, 2H, CH₂), 1.63–1.84 and 2.61–2.93(m, 2H, CH₂), 2.30(s, 3H, CH₃), 3.35–3.52(m, 2H, CH₂) | |
| H | (CH₂)₃O—[epoxide] | 1.33 | 2.99 | 1.05 | 7.09–7.34 | 3.41, 3.48 | 0.58(t, 2H, CH₂), 1.59–1.84 and 2.60–2.92(m, 2H, CH₂), 3.01–3.29(m, 1H, CH), 3.34–3.53(m, 4H, CH₂) | |
| H | (CH₂)₃O₂CC(=CH₂)Me | 1.33 | 2.98 | 1.05 | 7.08–7.36 | 3.38, 3.47 | 0.57(t, 2H, CH₂), 1.57–1.84(m, 2H, CH₂), 1.97(s, 3H, CH₃), 4.10(t, 2H, CH₂), 5.62–6.29(m, 2H, CH) | |
| H | [cyclohexenyl-ethyl] | 1.33 | 2.98 | 1.05 | 7.17–7.34 | 3.37, 3.47 | 0.45–0.65(m, 2H, CH₂), 1.47–2.21(m, 9H, CH₂ and CH), 5.51–5.73(m, 2H, CH) | |
| H | (CH₂)₃SiMe₃ | 1.33 | 3.00 | 1.06 | 7.10–7.35 | 3.35, 3.47 | 0.00(s, 9H, CH₃), 0.45–0.63, 0.61–0.63 and 1.53–1.64(m, 2H, CH₂) | |
| H | (CH₂)₃SiMe₃ | 1.32 | 2.99 | 1.05 | 7.08–7.35 | 3.34, 3.45 | –0.01(s, 9H, CH₃), 0.44–0.62(m, 4H, CH₂) | |
| H | (CH₂)₃SiMe₂OMe | 1.32 | 3.00 | 1.06 | 7.09–7.34 | 3.35, 3.48 | 0.09(s, 6H, CH₃), 0.44–0.61, 1.09–1.21 and 1.66–1.76(m, 2H, CH₂), 3.49(s, 3H, OCH₃) | |
| H | (CH₂)₂SiMe₂OMe | 1.33 | 3.00 | 1.06 | 7.10–7.37 | 3.34, 3.47 | 0.10(s, 6H, CH₃), 0.44–0.61 and 1.09–1.21(m, 2H, CH₂), 3.50(s, 3H, OCH₃) | |
| H | (CH₂)₃SiMe(OMe)₂ | 1.32 | 3.01 | 1.05 | 7.12–7.36 | 3.35, 3.48 | 0.10(s, 3H, CH₃), 0.44–0.62(m, 4H, CH₂) and 1.62–1.74(m, 2H, CH₂), 3.50(s, 6H, OCH₃) | |
| H | (CH₂)₂SiMe(OMe)₂ | 1.33 | 3.00 | 1.05 | 7.10–7.35 | 3.34, 3.47 | 0.09(s, 3H, CH₃), 0.45–0.62(m, 4H, CH₂), 3.49(s, 6H, OCH₃) | |
| H | (CH₂)₃Si(OMe)₃ | 1.32 | 3.01 | 1.06 | 7.09–7.34 | 3.35, 3.47 | 0.45–0.63(m, 4H, CH₂), 1.46–1.77(m, 2H, CH₂), 3.49(s, 9H, OCH₃) | |
| H | (CH₂)₂Si(OMe)₃ | 1.33 | 3.00 | 1.06 | 7.10–7.34 | 3.34, 3.46 | 0.44–0.61 and 1.44–1.64(m, 2H, CH₂), 3.48(s, 9H, OCH₃) | |
| 3-Me | (CH₂)₃Cl | 1.32 | 3.00 | 1.08 | 7.08–7.27 | 3.36, 3.47 | 0.45–0.60 and 1.70–1.80(m, 2H, CH₂), 2.37(s, 3H, CH₃), 3.39(t, 2H, CH₂) | |

TABLE III-continued

The structure and $^1$H-NMR data of 3-(aryl with one substituent)propyp-1,1-dimethoxysilanes

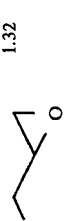

| R$_1$ | R | CH$_3$(d) | CH(hex.) | CL$_2$(d) | aryl-H (m) | OCH$_3$(s) | R$_1$ and R | Remark |
|---|---|---|---|---|---|---|---|---|
| 4-Me | (CH$_2$)$_3$Cl | 1.33 | 3.00 | 1.08 | 7.08–7.27 | 3.37, 3.47 | 0.45–0.60 and 1.70–1.80(m, 2H, CH$_2$), 2.39(s, 3H, CH$_3$), 3.39(t, 2H, CH$_2$) | |
| 3-Me | (CH$_2$)$_3$O⎯⌐○ | 1.32 | 2.98 | 1.05 | 7.03–7.32 | 3.41, 3.38 | 0.57(t, 2H, CH$_2$), 1.58–1.85 and 2.60–2.90(m, 2H, CH$_2$), 3.00–3.27(m, 1H, CH), 3.32–3.54(m, 4H, CH$_2$), 2.35(s, 3H, CH$_3$) | |
| 4-Me | (CH$_2$)$_3$O⎯⌐○ | 1.33 | 2.98 | 1.05 | 7.03–7.32 | 3.41, 3.38 | 0.58(t, 2H, CH$_2$), 1.58–1.85 and 2.60–2.90(m, 2H, CH$_2$), 3.00–3.27(m, 1H, CH), 3.33–3.54(m, 4H, CH$_2$), 2.36(s, 3H, CH$_3$) | |
| 3-Me | (CH$_2$)$_3$O$_2$CCH$_3$ | 1.32 | 2.99 | 1.05 | 7.02–7.29 | 3.42, 3.38 | 0.57(t, 2H, CH$_2$), 1.63–1.82 and 2.61–2.93(m, 2H, CH$_2$), 2.30(s, 3H, CH$_3$), 3.35–3.52(m, 2H, CH$_2$), 2.36(s, 3H, CH$_3$) | |
| 4-Me | (CH$_2$)$_3$O$_2$CCH$_3$ | 1.33 | 2.99 | 1.05 | 7.02–7.29 | 3.42, 3.38 | 0.57(t, 2H, CH$_2$), 1.63–1.82 and 2.61–2.93(m, 2H, CH$_2$), 2.30(s, 3H, CH$_3$), 3.35–3.52(m, 2H, CH$_2$), 2.37(s, 3H, CH$_3$) | |
| 3-Me | (CH$_2$)$_3$O$_2$CC=CH$_2$<br>　　　　　　　Me | 1.32 | 2.98 | 1.05 | 7.06–7.33 | 3.39, 3.47 | 0.57(t, 2H, CH$_2$), 1.55–1.84(m, 2H, CH$_2$), 1.97 and 2.36 (s, 3H, CH$_3$), 4.10(t, 2H, CH$_2$), 5.61–6.30(m, 2H, CH) | |
| 4-Me | (CH$_2$)$_3$O$_2$CC=CH$_2$<br>　　　　　　　Me | 1.33 | 2.98 | 1.05 | 7.06–7.33 | 3.40, 3.48 | 0.57(t, 2H, CH$_2$), 1.55–1.84(m, 2H, CH$_2$), 1.97 and 2.37 (s, 3H, CH$_3$), 4.11(t, 2H, CH$_2$), 5.61–6.30(m, 2H, CH) | |
| 3-Me | (CH$_2$)$_2$SiMe$_2$OMe | 1.32 | 2.98 | 1.05 | 7.06–7.37 | 3.36, 3.47 | 0.40(s, 6H, CH$_3$), 2.36(s, 3H, CH$_3$), 0.76–1.20(m, 4H, CH$_2$) | |
| 4-Me | (CH$_2$)$_2$SiMe$_2$OMe | 1.33 | 2.99 | 1.05 | 7.06–7.37 | 3.37, 3.47 | 0.41(s, 6H, CH$_3$), 2.37(s, 3H, CH$_3$), 0.76–1.20(m, 4H, CH$_2$) | |
| 3-Me | (CH$_2$)$_2$Si(OMe) | 1.33 | 2.99 | 1.06 | 7.08–7.31 | 3.35, 3.46 | 0.42–0.57(m, 4H, CH$_2$) and 2.37(s, 3H, CH$_3$), 3.48(s, 9H, OCH$_3$) | |
| 4-Me | (CH$_2$)$_2$Si(OMe) | 1.34 | 2.99 | 1.06 | 7.08–7.31 | 3.36, 3.47 | 0.42–0.56(m, 4H, CH$_2$) and 2.38(s, 3H, CH$_3$), 3.48(s, 9H, OCH$_3$) | |
| 3-Me | (CH$_2$)$_6$CH$_3$ | 1.32 | 2.99 | 1.06 | 7.06–7.29 | 3.34, 3.48 | 0.45–0.61(m, 2H, CH$_2$), 0.88(t, 3H, CH$_3$), 1.15–1.61(m, 8H, CH$_2$), 2.33(s, 3H, CH$_3$) | |
| 4-Me | (CH$_2$)$_6$CH$_3$ | 1.33 | 2.99 | 1.06 | 7.06–7.29 | 3.35, 3.49 | 0.45–0.61(m, 2H, CH$_2$), 0.88(t, 3H, CH$_3$), 1.10–1.35(m, 4H, CH$_2$), 1.56–1.89(m, 8H, CH$_2$), 2.34(s, 3H, CH$_3$) | |
| 3-Me | c-hexyl | 1.37 | 3.02 | 1.05 | 7.08–7.35 | 3.47, 3.50 | 0.56–0.68(m, 1H, CH), 1.10–1.35(m, 4H, CH$_2$), 1.56–1.89(m, 6H, CH$_2$), 2.34(s, 3H, CH$_3$) | |
| 4-Me | c-hexyl | 1.37 | 3.02 | 1.05 | 7.08–7.35 | 4.47, 3.49 | 0.56–0.68(m, 1H, CH), 1.10–1.35(m, 4H, CH$_2$), 1.56–1.89(m, 6H, CH$_2$), 2.35(s, 3H, CH$_3$) | |
| 3-Me | (CH$_2$)$_2$Ph | 1.32 | 2.99 | 1.05 | 7.05–7.34 | 3.37, 3.47 | 0.47–0.63 and 2.60–2.67(m, 2H, CH$_2$), 7.05–7.34(m, 5H, aryl-H), 2.34(s, 3H, CH$_3$) | Example 14 |
| 4-Me | (CH$_2$)$_2$Ph | 1.33 | 2.99 | 1.05 | 7.05–7.34 | 3.38, 3.48 | 0.47–0.63 and 2.60–2.67(m, 2H, CH$_2$), 7.05–7.34(m, 5H, aryl-H), 2.35(s, 3H, CH$_3$) | Example 14 |
| 3-Et | (CH$_2$)$_3$Cl | 1.33 | 2.99 | 1.07 | 7.04–7.27 | 3.35, 3.47 | 0.47–0.63 and 1.72–1.79(m, 2H, CH$_2$), 1.25(t, 3H, CH$_3$), 3.36(q, 2H, CH$_2$) | |

TABLE III-continued

The structure and $^1$H-NMR data of 3-(aryl with one substituent)propyp-1,1-dimethoxysilanes $$\text{Me} \quad \text{MeO} \quad \text{OMe}$$
$$R_1 - \text{C}_6\text{H}_4 - \text{CH}_2 - \text{CH}(\text{Me}) - \text{Si} - R$$

| Substituents | | | | | NMR data (ppm) | | | Remark |
|---|---|---|---|---|---|---|---|---|
| R$_1$ | R | CH$_3$(d) | CH(hex.) | CL$_2$(d) | aryl-H (m) | OCH$_3$(s) | R$_1$ and R | |
| 4-Et | (CH$_2$)$_3$Cl | 1.34 | 2.99 | 1.07 | 7.04-7.27 | 3.36, 3.48 | 0.47-0.63 and 1.72-1.79(m, 2H, CH$_2$), 1.26(t, 3H, CH$_3$), 3.37(q, 2H, CH$_2$) | |
| 4-Et | (CH$_2$)$_2$CH$_3$ | 1.31 | 2.97 | 1.05 | 7.01-7.28 | 3.36, 3.47 | 0.89 and 1.24(t, 3H, CH$_3$), 1.28-1.37(m, 2H, CH$_2$), 2.62(q, 2H, CH$_2$) | |
| 3-Et | (CH$_2$)$_2$Ph | 1.32 | 2.99 | 1.06 | 7.11-7.42 | 3.34, 3.48 | 0.58-0.86 and 1.67-1.76(m, 2H, CH$_2$), 2.79(q, 2H, CH$_2$), 7.11-7.42(m, 5H, Phenyl-H) | |
| 4-Et | (CH$_2$)$_2$Ph | 1.33 | 2.99 | 1.07 | 7.11-7.42 | 3.35, 3.49 | 0.58-0.86 and 1.67-1.76(m, 2H, CH$_2$), 2.80(q, 2H, CH$_2$), 7.11-7.42(m, 5H, Phenyl-H) | |
| 3-Et | (CH$_2$)$_2$SiMe(OMe)$_2$ | 1.33 | 3.00 | 1.06 | 7.09-7.30 | 3.35, 3.46 | 0.79 and 1.25(s, 3H, CH$_3$), 0.41-0.60(m, 4H, CH$_2$), 1.26(t, 3H, CH$_3$), 2.81(q, 2H, CH$_2$), 3.48(s, 9H, OCH$_3$) | |
| 4-Et | (CH$_2$)$_2$SiMe(OMe)$_2$ | 1.34 | 3.00 | 1.06 | 7.09-7.30 | 3.36, 3.46 | 0.80 and 1.26(s, 3H, CH$_3$), 0.41-0.60(m, 4H, CH$_2$), 1.27(t, 3H, CH$_3$), 2.82(q, 2H, CH$_2$), 3.49(s, 9H, OCH$_3$) | |
| 3-Et | (CH$_2$)$_2$Si(OMe)$_3$ | 1.33 | 2.99 | 1.05 | 7.05-7.30 | 3.35, 3.46 | 0.41-0.59(m, 4H, CH$_2$), 1.24(t, 3H, CH$_3$), 2.80(q, 2H, CH$_2$), 3.47(s, 9H, OCH$_3$) | |
| 4-Et | (CH$_2$)$_2$Si(OMe)$_3$ | 1.34 | 2.99 | 1.05 | 7.05-7.30 | 3.35, 3.47 | 0.41-0.59(m, 4H, CH$_2$), 1.25(t, 3H, CH$_3$), 2.81(q, 2H, CH$_2$), 3.48(s, 9H, OCH$_3$) | |
| 3-Et | (CH$_2$)$_6$CH$_3$ | 1.31 | 2.97 | 1.06 | 7.04-7.23 | 3.34, 3.47 | 0.47-0.59(m, 2H, CH$_3$), 0.88 and 1.24(t, 3H, CH$_3$), 1.13-1.60(m, 8H, CH$_2$), 2.80(q, 2H, CH$_2$) | |
| 4-Et | (CH$_2$)$_6$CH$_3$ | 1.32 | 2.96 | 1.06 | 7.04-7.25 | 3.34, 3.47 | 0.47-0.59(m, 2H, CH$_2$), 0.88 and 1.25(t, 3H, CH$_3$), 1.13-1.60(m, 8H, CH$_3$), 2.81(q, 2H, CH$_2$) | |
| 3-Et | c-hexyl | 1.35 | 3.01 | 1.06 | 7.03-7.32 | 3.46, 3.50 | 0.64-0.72(m, 1H, CH), 1.23(t, 3H, CH$_3$), 1.09-1.33(m, 4H, CH$_2$), 1.54-1.89(m, 6H, CH$_2$), 2.80(q, 2H, CH$_2$) | |
| 4-Et | c-hexyl | 1.36 | 3.01 | 1.06 | 7.03-7.32 | 3.47, 3.50 | 0.64-0.72(m, 1H, CH), 1.24(t, 2H, CH$_3$), 1.09-1.33(m, 4H, CH$_2$), 1.54-1.89(m, 6H, CH$_2$), 2.80(q, 2H, CH$_2$) | |
| 3-i-Pr | (CH$_2$)$_3$Cl | 1.32 | 3.00 | 1.07 | 6.95-7.28 | 3.36, 3.47 | 0.42-0.59 and 1.68-1.74(m, 2H, CH$_2$), 1.28(d, 6H, CH$_6$), 2.91(hept. 1H, CH), 3.36(t, 2H, CH$_2$) | |
| 4-i-Pr | (CH$_2$)$_3$Cl | 1.33 | 3.00 | 1.07 | 6.95-7.28 | 3.36, 3.48 | 0.42-0.59 and 1.68-1.74(m, 2H, CH$_2$), 1.28(d, 6H, CH$_6$), 2.92(hept. 1H, CH), 3.37(t, 2H, CH$_2$) | |
| 3-i-pr | (CH$_2$)$_6$CH$_3$ | 1.33 | 3.00 | 1.06 | 7.00-7.26 | 3.34, 3.47 | 0.40-0.57(m, 2H, CH$_2$), 0.87(t, 3H, CH$_3$), 1.11-1.60(m, 8H, CH$_2$), 1.24(d, 6H, CH$_3$), 2.89(hept., 1H, CH) | |
| 4-i-pr | (CH$_2$)$_6$CH$_3$ | 1.34 | 3.00 | 1.06 | 7.00-7.26 | 3.35, 3.47 | 0.40-0.57(m, 2H, CH$_2$), 0.87(t, 3H, CH$_3$), 1.11-1.60(m, 8H, CH$_2$), 1.25(d, 6H, CH$_3$), 2.91(hept, 1H, CH) | |
| 3-i-pr | (CH$_2$)$_2$Si(OMe)$_3$ | 1.33 | 2.99 | 1.05 | 7.00-7.35 | 3.34, 3.47 | 0.40-0.60(m, 4H, CH$_2$), 1.26(d, 6H, CH$_6$), 2.91(hept. 1H, CH), 3.47(s, 9H, OCH$_3$) | |
| 4-i-pr | (CH$_2$)$_2$Si(OMe)$_3$ | 1.34 | 3.00 | 1.06 | 7.00-7.35 | 3.35, 3.47 | 0.40-0.60(m, 4H, CH$_2$), 1.28(d, 6H, CH$_6$), 2.92(hept. 1H, CH), 3.48(s, 9H, OCH$_3$) | |
| 3-Ph | (CH$_2$)$_3$Cl | 1.32 | 3.00 | 1.06 | 7.17-7.61 | 3.36, 3.47 | 0.41-0.59 and 1.71-1.80(m, 2H, CH$_2$), 3.24(t, 2H, CH$_2$), 7.17-7.61(m, 5H, phenyl-H) | |
| 4-Ph | (CH$_2$)$_3$Cl | 1.33 | 3.00 | 1.06 | 7.17-7.61 | 3.36, 3.47 | 0.41-0.59 and 1.71-1.80(m, 2H, CH$_2$), 3.25(t, 2H, CH$_2$), 7.17-7.61(m, 5H, phenyl-H) | |
| 2-F | (CH$_2$)$_3$Cl | 1.32 | 3.01 | 1.06 | 7.01-7.28 | 3.36, 3.47 | 0.45-0.62(m, 2H, CH$_2$), 1.72-1.83(m, 2H, CH$_2$), 3.44(t, 2H, CH$_2$) | |
| 4-F | (CH$_2$)$_3$Cl | 1.35 | 3.01 | 1.06 | 7.01-7.28 | 3.36, 3.48 | 0.45-0.62(m, 2H, CH$_2$), 1.72-1.83(m, 2H, CH$_2$), 3.44(t, 2H, CH$_2$) | |
| 2-F | (CH$_2$)$_2$SiMe(OMe)$_2$ | 1.33 | 3.01 | 1.05 | 7.03-7.26 | 3.35, 3.46 | 0.41-0.59 and 1.47-1.59(m, 2H, CH$_2$), 3.50(s, 9H, OCH$_3$) | |

TABLE III-continued

The structure and $^1$H-NMR data of 3-(aryl with one substituent)propyp-1,1-dimethoxysilanes Structure: Me(MeO)(OMe)Si-CH2-CH(R)-CH2-C6H4-R1

| Substituents | | CH$_3$(d) | CH(hex.) | CL$_2$(d) | aryl-H (m) | OCH$_3$(s) | R$_1$ and R | Remark |
|---|---|---|---|---|---|---|---|---|
| R$_1$ | R | | | | | | | |
| 4-F | (CH$_2$)$_2$SiMe(OMe)$_2$ | 1.34 | 3.00 | 1.05 | 7.03–7.26 | 3.35, 3.47 | 1.11–1.27 and 1.67–1.75(m, 2H, CH$_2$), 3.50(s, 9H, OCH$_3$) | |
| 2-Cl | (CH$_2$)$_3$Cl | 1.32 | 3.51 | 1.05 | 7.11–7.42 | 3.35, 3.46 | 0.41–0.57 and 1.67–1.80(m, 2H, CH$_2$), 3.42(t, 2H, CH$_2$) | |
| 4-Cl | (CH$_2$)$_3$Cl | 1.33 | 3.00 | 1.05 | 7.11–7.42 | 3.37, 3.46 | 0.41–0.57 and 1.67–1.80(m, 2H, CH$_2$), 3.44(t, 2H, CH$_2$) | |
| 2-Cl | (CH$_2$)$_5$CH$_3$ | 1.32 | 3.50 | 1.04 | 7.09–7.38 | 3.34, 3.47 | 0.41–0.58(m, 2H, CH$_2$), 0.88(t, 3H, CH$_3$), 1.23–1.44(m 8H, CH$_2$,) | |
| 4-Cl | (CH$_2$)$_5$CH$_3$ | 1.33 | 2.99 | 1.04 | 7.09–7.38 | 3.34, 3.48 | 0.41–0.58(m, 2H, CH$_2$), 0.88(t, 3H, CH$_3$), 1.23–1.44(m 8H, CH$_2$,) | |
| 2-Cl | (CH$_2$)$_2$Si(OMe)$_3$ | 1.32 | 3.43 | 1.04 | 7.07–7.34 | 3.34, 3.46 | 0.42–0.61(m, 4H, CH$_2$), 3.48(s, 9H, OCH$_3$) | |
| 4-Cl | (CH$_2$)$_2$Si(OMe)$_3$ | 1.33 | 3.00 | 1.04 | 7.07–7.34 | 3.34, 3.47 | 0.42–0.61(m, 4H, CH$_2$), 3.49(s, 9H, OCH$_3$) | |
| 2-Br | (CH$_2$)$_3$Cl | 1.32 | 3.44 | 1.05 | 7.03–7.45 | 3.33, 3.46 | 0.42–0.61 and 1.68–1.87(m, 2H, CH$_2$), 3.42(t, 2H, CH$_2$) | |
| 4-Br | (CH$_2$)$_3$Cl | 1.33 | 2.99 | 1.05 | 7.03–7.45 | 3.34, 3.46 | 0.42–0.61 and 1.68–1.87(m, 2H, CH$_2$), 3.43(t, 2H, CH$_2$) | |
| 2-Br | (CH$_2$)$_2$SiMe$_3$ | 1.33 | 3.47 | 1.05 | 7.04–7.46 | 3.33, 3.46 | 0.40–0.68(m, 4H, CH$_2$), 3.48(s, 9H, OCH$_3$) | |
| 4-Br | (CH$_2$)$_2$SiMe$_3$ | 1.34 | 3.00 | 1.05 | 7.04–7.46 | 3.34, 3.47 | 0.40–0.68(m, 4H, CH$_2$), 3.49(s, 9H, OCH$_3$) | |

EXAMPLE 15

In the same apparatus and procedures as EXAMPLE 1, 12.7 g (0.049 mole) of 3-(2,5-dimethylphenyl)-1,1-dimethoxy-1-silabutane, 13.1 g (0.15 mole) of 1-hexene, and 90 μl of 1% chloroplatinic acid in isopropanol were placed under the dry nitrogen atmosphere. The reactor was refluxed for 3 hours. Vacuum distillation of the reaction products gave 9.4 g (bp, 131°–3° C./0.6 mmHg) of 4,4-dimethoxy-2-(2,5-dimethylphenyl)-4-siladecane.

EXAMPLE 16

In the same apparatus and procedures as EXAMPLE 1, 10.0 g (0.046 mole) of 3-phenyl-1,1-dimethoxy-1-silabutane, 3.7 g (0.07 mole) of acrylonitrile, and 0.3 g of nickel metal obtained from the reduction of nickel iodide with metallic sodium were placed under the dry nitrogen atmosphere. The reactor was refluxed for 3 hours. Vacuum distillation of the reaction products gave 9.0 g (bp, 120°–2° C./0.6 mmHg) of 1-cyano-3,3-dimethoxy-5-phenyl-3-silahexane.

The structures and NMR data of the compounds prepared using the same procedure as described in EXAMPLE 15 and 16 are listed in Table IV.

TABLE IV

The structure and $^1$H-NMR data of 3-(aryl with two substituents)propyldimethoxysilanes

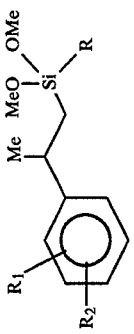

| Substituents | | | | | | | | | |
|---|---|---|---|---|---|---|---|---|---|
| R$_1$ | R$_2$ | R | CH$_3$(d) | CH(hex.) | CH$_2$(d) | aryl-H (m) | OCH$_3$ | R$_1$, R$_2$ and R | |
| 2-Me | 5-Me | (CH$_2$)$_3$Cl | 1.36 | 3.05 | 1.06 | 7.12–7.28 | 3.35, 3.48 | 0.42–0.63 (m, 2H, CH$_2$), 1.67–1.78(m, 2H, CH$_2$), 2.34 and 2.36(s, 3H, CH$_3$), 3.38(t, 2H, CH$_2$) | |
| 2-Me | 5-Me | (CH$_2$)$_5$CH$_3$ | 1.32 | 3.05 | 1.05 | 6.98–7.24 | 3.34, 3.48 | 0.41–0.61(m, 2H, CH$_2$), 0.88(s, 3H, CH$_3$), 1.16–1.31(m, 8H, CH$_2$), 2.31 and 2.33(s, 3H, CH$_3$) | Example 15 |
| 2-Me | 5-Me | (CH$_2$)$_{17}$CH$_3$ | 1.32 | 3.04 | 1.05 | 6.97–7.25 | 3.34, 3.48 | 0.40–0.61(m, 2H, CH$_2$), 0.88(s, 3H, CH$_3$), 1.16–1.32(m, 36H, CH$_2$), 2.31 and 2.32(s, 3H, CH$_3$) | |
| 3-Me | 4-Me | (CH$_2$)$_2$Ph | 1.34 | 3.04 | 1.04 | 7.01–7.41 | 3.35, 3.48 | 0.48–0.70 and 2.61–2.71(m, 2H, CH$_2$), 2.31 and 2.32(s, 3H, CH$_3$), 7.01–7.41(m, 5H, phenyl-H) | |
| 3-Me | 4-Me | (CH$_2$)$_2$CN* | 1.35 | 3.05 | 1.05 | 7.08–7.38 | 3.34, 3.48 | 0.50–0.63(m, 2H, CH$_2$), 2.32 and 2.34(s, 3H, CH$_3$), 2.46(t, 2H, CH$_2$) | |
| 2-Me | 5-Me | c-hexyl | 1.34 | 3.05 | 1.05 | 7.15–7.37 | 3.35, 3.46 | 0.43–0.59(m, 1H, CH), 1.10–1.34(m, 4H, CH$_2$), 1.56–1.93(m, 6H, CH$_2$), 2.33 and 2.34(s, 3H, CH$_3$) | |
| 2-Me | 5-Me | (CH$_2$)$_3$O$_2$CCH$_3$ | 1.34 | 3.00 | 1.05 | 7.02–7.29 | 3.39, 3.38 | 0.56(t, 2H, CH$_2$), 1.63–1.82 and 2.61–2.93(m, 2H, CH$_2$), 2.29, 2.36 and 2.37(s, 3H, CH$_3$), 3.35–3.53(m, 2H, CH$_2$) | |
| 2-Me | 5-Me | (CH$_2$)$_2$SiMe$_2$OMe | 1.35 | 3.00 | 1.05 | 7.06–7.27 | 3.34, 3.47 | 0.02(s, 6H, CH$_3$) 0.43–0.64(m, 4H, CH$_2$), 2.34 and 2.35(s, 3H, CH$_3$), 3.50(s, 3H, CH$_3$) | |
| 2-Me | 5-Me | (CH$_2$)$_2$SiMe(OMe)$_2$ | 1.34 | 3.00 | 1.05 | 7.07–7.28 | 3.34, 3.46 | 0.07(s, 3H, CH$_3$), 0.42–0.63 and 1.46–1.63(m, 2H, CH$_2$), 2.35 and 2.38(s, 3H, CH$_3$), 3.49(s, 6H, CH$_3$) | |
| 2-Me | 5-Me | (CH$_2$)$_2$Si(OMe)$_3$ | 1.34 | 3.01 | 1.05 | 7.03–7.29 | 3.34, 3.46 | 0.41–0.61(m, 4H, CH$_2$), 2.35 and 2.37(s, 3H, CH$_3$), 3.49(s, 6H, CH$_3$) | |
| 2-Me | 5-Me | (CH$_2$)$_3$O$_2$CC=CH$_2$ \| Me | 1.33 | 2.99 | 1.05 | 7.03–7.34 | 3.38, 3.45 | 0.56(t, 2H, CH$_2$), 1.56–1.81(m, 2H, CH$_2$), 1.97, 2.35 and 2.37 (s, 3H, CH$_3$), 4.09(t, 2H, CH$_2$), 5.60–6.29(m, 2H, CH) | |
| 2-Me | 5-Me | (CH$_2$)$_3$O⌒⌐O | 1.33 | 2.99 | 1.05 | 7.03–7.34 | 3.39, 3.38 | 0.56(t, 2H, CH$_2$), 1.58–1.84 and 2.60–2.89(m, 2H, CH$_2$), 3.00–3.25 (m, 1H, CH), 3.302–3.52(m, 4H, CH$_2$), 2.35, 2.36(s, 3H, CH$_3$) | |
| 2,3-dibenzo | | (CH$_2$)$_3$Cl | 1.38 | 3.67 | 1.10 | 7.22–8.26 | 3.39, 3.51 | 0.52–0.71 and 1.63–1.87(m, 2H, CH$_2$), 3.36(t, 2H, CH$_2$), 7.22–8.26(m, 4H, (CH)$_4$) | |
| 3,4-dibenzo | | (CH$_2$)$_3$Cl | 1.36 | 3.67 | 1.10 | 7.22–8.26 | 3.38, 3.50 | 0.52–0.71 and 1.63–1.87(m, 2H, CH$_2$), 3.35(t, 2H, CH$_2$), 7.22–8.26(m, 4H,(CH)$_4$) | |

*Nickel metal used as the catalyst

What is claimed is:

1. 2-Arylpropyl)alkylsilanes represented by the formula III;

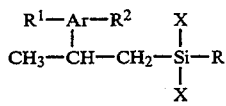

wherein, $R^1$ and $R^2$ represent independently hydrogen, alkyl ($C_1$-$C_4$), fluoro, chloro or bromo; Ar represents a phenyl ring, naphthalene ring or biphenyl ring; X represents hydrogen, chloro, or methoxy; R represents —$(CH_2CH_2)$—$R^3$, sec-butyl or cyclohexyl wherein $R^3$ is Ph, $CH_2Cl$, $C_nH_{2n}CH_3$ (n=0-15), $CH_2Si(Me)_mCl_{3-m}$ (m=0-3), $(CH_2)_2Si(Me)_m(OMe)_{3-m}$ (m=0-3), $(CH_2)_3Si(Me)_m(OMe)_{3-m}$ (m=0-3), $Si(Me)_mCl_{3-m}$ (m=0-3), $CF_3$, $CN$, $CH_2CN$,

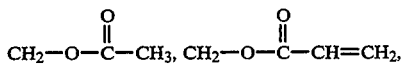

$CH=CH_2$, or $(CH_2)_4CH=CH_2$,

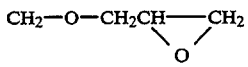

or Ph—$CH_2Cl$.

2. A method for preparing (2-arylpropyl)alkylsilanes represented by the formula III, comprising reacting (2-arylpropyl)silanes represented by the formula II with olefin compounds represented by the formula I in the presence of hydrosilation catalyst;

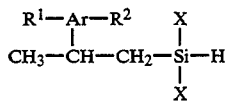

wherein R, $R^1$, $R^2$, $R^3$, Ar and X are the same group as defined in claim 1.

3. The compounds in accordance with claim 1, wherein $R^1$ is hydrogen, X is Cl or methoxy, $R^2$ is hydrogen, methyl, ethyl, isopropyl, halogen, or phenyl and R is chloropropyl.

4. The compounds in accordance with claim 1, wherein $R^1$ is hydrogen, X is Cl or methoxy, $R^2$ is hydrogen, methyl, ethyl, isopropyl, halogen, or phenyl and R is cyclorohexyl.

5. The compounds in accordance with claim 1, wherein $R^1$ is hydrogen, X is Cl or methoxy, $R^2$ is hydrogen, methyl, ethyl, isopropyl, halogen, or phenyl, and R is 2-cyanoethyl or 3-cyanopropyl.

6. The compounds in accordance with claim 1, wherein $R^1$ is hydrogen, X is Cl or methoxy, $R^2$ is hydrogen, methyl, ethyl, isopropyl, halogen, or phenyl, and R is 2-butenyl or 8-octenyl.

7. The compounds in accordance with claim 1, wherein $R^1$ is hydrogen, X is Cl or methoxy, $R^2$ is hydrogen, methyl, ethyl, isopropyl, halogen, or phenyl, and R is 2-phenyethyl or 2-(4-chlorophenyl)ethyl.

8. The compounds in accordance with claim 1, wherein $R^1$ is hydrogen, X is Cl or methoxy, $R^2$ is hydrogen, methyl, ethyl, isopropyl, halogen, or phenyl, and R is trifluoropropyl or trifluorobutyl.

9. The compounds in accordance with claim 1, wherein $R^1$ is hydrogen, X is Cl or methoxy, $R^2$ is hydrogen, methyl, ethyl, isopropyl, halogen, or phenyl, and R is 2-(2-cyclohexenyl)ethyl.

10. The compounds in accordance with claim 1, wherein $R^1$ is hydrogen, X is Cl or methoxy, $R^2$ is hydrogen methyl, ethyl, isopropyl, halogen, or phenyl, and R is $C_nH_{2n}CH_3$ (n=2-17).

11. The compounds in accordance with claim 1, wherein $R^1$ is hydrogen, X is Cl or methoxy, $R^2$ is hydrogen, methyl, ethyl, isopropyl, halogen, or phenyl, and R is 3-acetoxypropyl.

12. The compounds in accordance with claim 1, wherein $R^1$ is hydrogen, X is Cl or methoxy, $R^2$ is hydrogen, methyl, ethyl, isopropyl, halogen, or phenyl, and R is 3-(glycidoxy)propyl.

13. The compounds in accordance with claim 1, wherein $R^1$ is hydrogen, X is Cl or methoxy, $R^2$ is hydrogen, methyl, ethyl, isopropyl, halogen, or phenyl, and R is 3-*acryloxy)propyl.

14. The compounds in accordance with claim 1, wherein $R^1$ is hydrogen, X is Cl or methoxy, $R^2$ is hydrogen methyl, ethyl, isopropyl, halogen, or phenyl, and R is $(CH_2)_2Si(Me)_m Cl_{3-m}$ (m=0-3).

15. The compounds in accordance with claim 1, wherein $R^1$ is hydrogen, X is Cl or methoxy, $R^2$ is hydrogen, methyl, ethyl, isopropyl, halogen, or phenyl, and R is $(CH_2)_2Si(Me)_m(OME)_{3-m}$ (m=0-3) or $(CH_2)_3Si(Me)_m(OMe)_{3-m}$ (m=0-3).

16. The method in accordance with claim 2, wherein Ar is benzene, X is Cl or methoxy, and both of $R^1$ and $R^2$ are hydrogen.

17. The method in accordance with claim 2, wherein Ar is benzene and X is Cl or methoxy, $R^1$ is hydrogen, and $R^2$ is is methyl.

18. The method in accordance with claim 2, wherein Ar is benzene, X is Cl or methoxy, $R^1$ is hydrogen, and $R^2$ is ethyl.

19. The method in accordance with claim 2, wherein Ar is benzene, X is Cl or methoxy, $R^1$ is hydrogen, and $R^2$ is isopropyl.

20. The method in accordance with claim 2, wherein Ar is benzene, X is Cl or methoxy, $R^1$ is hydrogen, and $R^2$ is halogen.

21. The method in accordance with claim 2, wherein Ar is benzene, X is Cl or methoxy, $R^1$ is hydrogen, and $R^2$ is phenyl.

22. The method in accordance with claim 2, wherein Ar is benzene, X is Cl or methoxy, and both of $R^1$ and $R^2$ are independently alkyl ($C_1$-$C_4$).

23. The method in accordance with claim 2, wherein Ar is naphthalene, X is Cl or methoxy, and both of $R^1$ and $R^2$ are hydrogen.

24. The method in accordance with claim 2, wherein said compound is cyclohexene.

25. The method in accordance with claim 2, wherein said compound is allylglycidyl ether.

26. The method in accordance with claim 2, wherein said compound is allylacryl ester or allylacetyl ester.

27. The method in accordance with claim 2, wherein $R^3$ of the olefin compound is $C_nH_{2n}CH_3$ (n=0-15).

28. The method in accordance with claim 2, wherein $R^3$ of the olefin compound is $Si(Me)_mCl_{3-m}$ (m=0-3) or $(CH_2)Si(Me)_mCl_{3-m}$ (m=0-3).

29. The method in accordance with claim 2, wherein $R^3$ of the olefin compound is $Si(Me)_m(OMe)_{3-m}$ (m=0-3) or $(CH_2)Si(Me)_m(OMe)_{3-m}$ (m=0-3).

30. The method in accordance with claim 2, wherein the reaction temperature is from 30° C. to 160° C.

31. The method in accordance with claim 2, wherein said catalyst is 0.001-2% of chloroplatinic acid based on allylchlorosilane.

* * * * *